US006682929B2

(12) United States Patent
Brough et al.

(10) Patent No.: US 6,682,929 B2
(45) Date of Patent: Jan. 27, 2004

(54) ADENOVECTOR COMPLEMENTING CELLS

(75) Inventors: Douglas E. Brough, Gaithersburg, MD (US); Jason G. D. Gall, Germantown, MD (US); Imre Kovesdi, Rockville, MD (US)

(73) Assignee: GenVec, Inc., Gaithersburg, MD (US)

( * ) Notice: Subject to any disclaimer, the term of this patent is extended or adjusted under 35 U.S.C. 154(b) by 0 days.

(21) Appl. No.: 09/910,828

(22) Filed: Jul. 23, 2001

(65) Prior Publication Data

US 2003/0054553 A1 Mar. 20, 2003

(51) Int. Cl.$^7$ .......................... C12N 5/10; C12N 15/861
(52) U.S. Cl. ................... 435/371; 435/320.1; 435/325; 435/366
(58) Field of Search .................. 435/320.1, 455, 435/456, 457, 325, 366, 371, 5, 6

(56) References Cited

U.S. PATENT DOCUMENTS

| | | |
|---|---|---|
| 5,994,128 A | 11/1999 | Fallaux et al. |
| 6,033,908 A | 3/2000 | Bout et al. |
| 6,040,174 A | 3/2000 | Imler et al. |
| 6,127,175 A | 10/2000 | Vigne et al. |

FOREIGN PATENT DOCUMENTS

| | | |
|---|---|---|
| WO | WO 94/28152 A | 12/1994 |
| WO | WO 95/02697 A | 1/1995 |
| WO | WO 96/14061 A | 5/1996 |
| WO | WO 96/18418 A | 6/1996 |
| WO | WO 97/00326 A | 1/1997 |

OTHER PUBLICATIONS

Horvath et al., *Virology*, 184 (1), 141–148 (Sep. 1991).
Brough et al., *J. Virol.*, 70 (9), 6497–6501 (Sep. 1996).
Imler et al., *Gene Ther.*, 3 (1), 75–84 (Jan. 1996).
Wang et al., *Gene Ther.*, 2 (10), 775–783 (Dec. 1995).
Yeh et al., *J. Virol.*, 70 (1), 559–565 (Jan. 1996).

*Primary Examiner*—David Guzo
(74) *Attorney, Agent, or Firm*—Leydig, Voit & Mayer, Ltd.

(57) ABSTRACT

The invention provides cells, particularly NCI-H460 cells and Calu-1 cells, for the propagation of replication-deficient adenoviral vectors. The cells are lung carcinomas with either a wild-type p53 gene or a heterozygous K-ras mutation. The cells comprise at least one adenoviral nucleic acid sequence, which upon expression produces a gene product that complements for at least one essential gene function of one or more regions of an adenoviral genome so as to propagate a replication-deficient adenoviral vector comprising an adenoviral genome deficient in the at least one essential gene function of the one or more regions when present in the cell.

14 Claims, No Drawings

ADENOVECTOR COMPLEMENTING CELLS

FIELD OF THE INVENTION

This invention pertains to cells for the propagation of adenoviral vectors.

BACKGROUND OF THE INVENTION

Recombinant eukaryotic viral vectors have become a preferred means of gene transfer for many researchers and clinicians. The human adenovirus is one of the most widely used recombinant viral vectors in current gene therapy protocols. As the use of adenoviral vectors becomes more prevalent, the need for systems that efficiently produce adenoviral vectors suitable for administration is increasingly important.

A concern associated with recombinant adenoviral vectors is uncontrolled propagation of the vector upon administration. To address this concern, replication-deficient adenoviral vectors, typically lacking the essential E1 region of the adenoviral genome, have been developed. The relatively small foreign gene insert capacity of E1-deleted adenoviral vectors has led to the development of adenoviral vectors with additional early region gene deletions, particularly deletions in the E4 region (see, e.g., WO 96/18418 and U.S. Pat. No. 6,127,175). Such vectors are propagated in complementing cell lines expressing adenoviral E1 and E4 gene products, such as those described by Wang et al., *Gene Ther.,* 2, 775–783 (1995), and Yeh et al., *J. Virol.,* 70, 559–565 (1996).

Adenoviral vector technology is also limited by the difficulties associated with large-scale propagation of adenoviral vectors using currently available complementing cell lines. For example, while the A549 cell line supports sufficient propagation of wild-type adenovirus, adenoviral propagation is significantly reduced or nonexistent when A549 cells are engineered to constitutively express E1 gene products for complementation (see, e.g., Imler et al., *Gene Ther.,* 1, 75–84 (1996), and Gao et al., *Human Gene Ther.,* 11, 213–219 (2000)). Moreover, propagation of wild-type adenovirus on the widely used HEK 293 cell line (Graham et al., *J. Gen. Virol.,* 36, 59–72 (1977)) results in approximately 50–75% of the yield of wild-type adenovirus on A549 cells.

Accordingly, there remains a need for alternative cells for propagating replication-deficient adenoviral vectors. The invention provides such cells. These and other advantages of the invention, as well as additional inventive features, will be apparent from the description of the invention provided herein.

BRIEF SUMMARY OF THE INVENTION

The invention provides a cell having a cellular genome comprising at least one adenoviral nucleic acid sequence, which upon expression produces a gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell. The cell (i) is a pleural effusion, large cell lung carcinoma, (ii) is epithelial, and (iii) comprises a wild-type p53 gene. Alternatively, the cell (i) is a lung carcinoma, (ii) comprises a homozygous deletion of the p53 gene, and (iii) is heterozygous for a K-ras codon 12 mutation. The inventive cell preferably is an NCI-H460 cell or a Calu-1 cell.

The invention also provides a system comprising the inventive cell and a replication-defective adenoviral vector comprising an adenoviral genome deficient in the at least one essential gene function of the one or more regions. The invention further provides a method of propagating a replication-deficient adenoviral vector, wherein the method comprises providing the inventive cell, introducing a replication-deficient adenoviral vector into the inventive cell, and maintaining the cell to propagate the replication-deficient adenoviral vector.

DETAILED DESCRIPTION OF THE INVENTION

The invention provides a cell having a cellular genome comprising at least one adenoviral nucleic acid sequence, which upon expression produces a gene product that complements in trans for a deficiency in at least one essential gene function of one or more regions of an adenoviral genome of a replication-deficient adenoviral vector so as to propagate (i.e., replicate the entire life cycle of, or replicate to any stage of the life cycle of) the replication-deficient adenoviral vector when present in the cell.

The cell (i) is a large cell lung carcinoma derived from a pleural effusion (i.e., a pleural effusion, large cell lung carcinoma), (ii) is epithelial, and (iii) comprises a wild-type p53 gene. By "derived" from a pleural effusion is meant that the cell is isolated from a large cell lung carcinoma that originated from an effusion of the lung pleura. By "epithelial" is meant that the cell participates in lining the inner and outer surfaces of the organism from which it is isolated. The cell has a wild-typep53 gene in that the nucleic acid sequence encoding the p53 gene does not comprise any alterations that change the normal function of the p53 gene product in the inventive cell. Advantageously, the cell comprises a homozygous K-ras codon 12 mutation. The cell comprises a homozygous K-ras codon 12 mutation in that both alleles of the K-ras gene locus are mutated in the inventive cell. Moreover, the cell does not express the p16INK4a protein. The cell also desirably exhibits adherent growth in culture, and comprises two X chromosomes and two Y chromosomes.

The cell alternatively (i) is a lung carcinoma, (ii) comprises a homozygous deletion of the p53 gene, and (iii) is heterozygous for a K-ras codon 12 mutation. The cell comprises a homozygous deletion of the p53 gene in that both alleles of the p53 gene locus comprise deletions which, for example, prevent expression of the p53 gene product or render the p53 gene product non-functional. The cell is heterozygous for a K-ras codon 12 mutation in that the cell comprises a K-ras gene locus comprising a wild-type allele and a codon 12 mutation in the other allele. Advantageously, the cell does not express the p16INK4a protein. The cell also desirably exhibits adherent growth in culture. Desirably, the antigen expression profile of the cell comprises (i) blood type A, (ii) Rh positive, and (iii) HLA antigens A10, A11, B15, and Bw35. By "antigen expression profile" is meant the collection of antigens that are expressed on the surface of the inventive cell.

The cell can be any suitable such cell into which can be incorporated and preferably retained the adenoviral nucleic acid encoding at least one gene product which complements in trans for a deficiency in at least one essential gene function of one or more regions of an adenoviral genome. The cell desirably can propagate adenoviral vectors and/or adeno-associated viral (AAV) vectors when infected with such vectors or with nucleic acid sequences encoding the adenoviral or AAV genome. Most preferably, the cell can propagate a suitable replication-deficient adenoviral vector upon infection with an appropriate replication-deficient adenoviral vector or transfection with an appropriate replication-deficient viral genome. The cell preferably is an NCI-H460 cell or a Calu-1 cell having a cellular genome comprising at least one adenoviral nucleic acid sequence, which upon expression produces a gene product that complements in trans for a deficiency in at least one essential gene function of one or more regions of an adenoviral genome of a replication-deficient adenoviral vector so as to propagate the replication-deficient adenoviral vector when present in the cell.

Particularly desirable cell types are those that support high levels of wild-type adenovirus propagation. The cell desirably produces at least about 100% more wild-type adenovirus, preferably at least about 200% more wild-type adenovirus, and most preferably at least about 300% more wild-type adenovirus, than a 293 cell. The cell also desirably produces at least about 90% more wild-type adenovirus, more preferably at least about 100% more wild-type adenovirus, and most preferably at least about 130% more wild-type adenovirus, than an A549 cell. The cell preferably produces at least about 8,000 focus-forming units (FFU) per cell. More preferably, the cell produces at least about 15,000 FFU per cell. Most preferably, the cell produces at least about 30,000 (e.g., at least about 35,000, 40,000, 50,000, or more) FFU per cell.

The cell comprises at least one adenoviral nucleic acid sequence as described herein, i.e., the cell can comprise one adenoviral nucleic acid sequence as described herein or more than one adenoviral nucleic acid sequence as described herein (i.e., two or more adenoviral nucleic acid sequences). Such cell lines can be generated in accordance with standard molecular biological techniques as described in International Patent Application WO 95/34671 and U.S. Pat. No. 5,994,106. The adenoviral nucleic acid sequence preferably is stably integrated into the nuclear genome of the cell. The adenoviral nucleic acid sequence preferably is retained in the cellular genome (and the adenoviral nucleic acid sequence, upon expression, preferably produces a gene product complementing in trans for a deficiency in at least one essential gene function of one or more regions of an adenoviral genome) for at least about 10, more preferably at least about 20, passages in culture (e.g., at least about 30, 40, 100, or more passages). Not to adhere to any particular theory, it is believed that genomic integration of the adenoviral nucleic acid sequence encoding the complementing factor is required to generate stable cell lines for adenoviral vector production. Additionally, complementation by transient transfection employs both labor-intensive and inconsistent techniques, resulting in low adenovirus yield and difficulty associated with large-scale viral production. Although stable integration of the adenoviral nucleic acid sequence is preferred, the adenoviral nucleic acid sequence can reside, for example, on a plasmid, liposome, or any other type of molecule that can harbor an adenoviral nucleic acid sequence extrachromosomally. The introduction and stable integration of the adenoviral nucleic acid sequence into the genome of the cell requires standard molecular biology techniques that are well within the skill of the art, such as those described in Sambrook et al., *Molecular Cloning, a Laboratory Manual,* 2d ed., Cold Spring Harbor Press, Cold Spring Harbor, N.Y. (1989), Watson et al., *Recombinant DNA,* 2d ed., Scientific American Books (1992), and Ausubel et al., *Current Protocols in Molecular Biology,* Wiley Interscience Publishers, NY (1995).

The "adenoviral nucleic acid sequence" can be any nucleic acid sequence that is obtained from, derived from, or based upon an adenoviral nucleic acid sequence. A sequence is "obtained" from a source when it is isolated from that source. A sequence is "derived" from a source when it is isolated from a source but modified in any suitable manner (e.g., by deletion, substitution (mutation), insertion, or other modification to the sequence) so as not to disrupt the normal function of the source gene. A nucleic acid sequence is "based upon" a source when the sequence is a sequence more than about 70% homologous (preferably more than about 80% homologous, more preferably more than about 90% homologous, and most preferably more than about 95% homologous) to the source but obtained through synthetic procedures (e.g., polynucleotide synthesis, directed evolution, etc.). Identifying such homologous sequences can be accomplished using any suitable method, particularly through use of the GenBank sequence databases provided by the National Center for Biotechnology Information (NCBI). Determining the degree of homology, including the possibility for gaps, can be accomplished using any suitable method (e.g., BLASTnr, provided by GenBank).

The adenoviral nucleic acid sequence can be obtained or derived from the same or different serotype of adenovirus as the adenoviral vector to be propagated in the cell. The adenoviral nucleic acid sequence and the adenoviral vector preferably are obtained from a group C adenovirus, more preferably from a serotype 2 or 5 adenovirus. Moreover, the adenoviral nucleic acid sequence can include one or more mutations (e.g., point mutations, deletions, insertions, etc.) from the corresponding naturally occurring adenoviral coding sequence. Thus, where mutations are introduced in the adenoviral nucleic acid sequence to effect one or more amino acid substitutions in an encoded gene product, such mutations desirably effect such amino acid substitutions whereby codons encoding positively-charged residues (H, K, and R) are substituted with codons encoding positively-charged residues, codons encoding negatively-charged residues (D and E) are substituted with codons encoding negatively-charged residues, codons encoding neutral polar residues (C, G, N, Q, S, T, and Y) are substituted with codons encoding neutral polar residues, codons encoding neutral non-polar residues (A, F, I, L, M, P, V, and W) are substituted with codons encoding neutral non-polar residues. Such mutations can also be introduced to effect one or more amino acid substitutions in the N- or C-terminus of the encoded non-adenoviral gene product.

The adenoviral nucleic acid sequence can be any suitable nucleic acid sequence as described herein that, upon expression, produces one or more gene products that complement for one or more deficiencies in any adenoviral essential gene functions (i.e., functions necessary for adenovirus propagation). By "complements for a deficiency in an essential gene function of an adenoviral genome" is meant that the gene product encoded by the adenoviral nucleic acid sequence exhibits an adenoviral gene function that is essential (i.e., necessary) for an adenoviral vector to propagate in a cell. For example, the gene product can induce transcription of promoters regulated by the E1A protein, such as the E2A promoter.

The gene product encoded by the adenoviral nucleic acid sequence can be an RNA sequence or a protein (e.g., a peptide or a polypeptide). Preferably, the gene product encoded by the adenoviral nucleic acid sequence is a protein.

The adenoviral nucleic acid sequence, upon expression, produces at least one gene product that provides an adenoviral essential gene function, i.e., that complements in trans for one or more deficiencies in any adenoviral essential gene function (i.e., a function that is necessary for adenovirus propagation). The adenoviral nucleic acid sequence, upon expression, can produce a gene product that complements for two or more deficiencies in adenoviral essential gene functions (from the same or different regions of the adenoviral genome). The adenoviral nucleic acid sequence, upon expression, can produce two or more gene products, each of which complements for a deficiency (i.e., at least one deficiency, including but not limited to, two or more deficiencies) in adenoviral essential gene functions (from the same or different regions of the adenoviral genome).

Essential adenoviral gene functions are those gene functions that are required for propagation (i.e., replication) of a replication-deficient adenoviral vector. Essential gene functions are encoded by, for example, the adenoviral early regions (e.g., the E1, E2, and E4 regions), late regions (e.g., the L1–L5 regions), genes involved in viral packaging (e.g., the IVa2 gene) and virus-associated RNAs (e.g., VA-RNA I and/or VA-RNA II). Thus, the gene product encoded by the adenoviral nucleic acid sequence complements for a deficiency in at least one adenoviral essential gene function encoded by the early regions, late regions, viral packaging regions, virus-associated RNA regions, or combinations thereof, including all adenoviral functions (e.g., to enable propagation of adenoviral amplicons comprising only inverted terminal repeats (ITRs) and the packaging signal or only ITRs and an adenoviral promoter).

The gene product desirably complements for a deficiency in at least one essential gene function of one or more regions of the adenoviral genome selected from the early regions, e.g., the E1, E2, and E4 regions. Preferably, the gene product complements in trans for a deficiency in at least one essential gene function of the E1 region of the adenoviral genome. More preferably, the gene product complements in trans for a deficiency in at least one essential gene function of an adenoviral E1A coding sequence and/or an adenoviral E1B coding sequence (which together comprise the E1 region). In that respect, one gene product can complement in trans for a deficiency in at least one essential gene function of the E1A coding sequence and another (i.e., different) gene product can complement in trans for a deficiency in at least one essential gene function of the E1B coding sequence. In addition or alternatively to the gene product(s) complementing in trans for the aforementioned deficiencies in adenoviral essential gene functions, the same or different gene product (s) can complement for a deficiency in at least one essential gene function of the E2 (particularly the adenoviral DNA polymerase and terminal protein) and/or E4 regions of the adenoviral genome. Desirably, a cell that complements for a deficiency in the E4 region comprises the E4-ORF6 gene sequence and produces the E4-ORF6 protein. Such a cell desirably comprises at least ORF6 and no other ORF of the E4 region of the adenoviral genome.

Although not preferred, a helper virus can be provided to the cell in the event that the cell does not complement for all deficiencies in essential gene functions of the adenoviral genome of the adenoviral vector to be propagated. The helper virus contains coding sequences that, upon expression, produce gene products which provide in trans those gene functions that are necessary for adenoviral propagation (e.g., the IVa2 gene function). In other words, the helper virus can comprise any adenoviral nucleic acid sequence that is not required in cis (e.g., the ITRs and packaging signal) for propagation.

The cell can further comprise an "enhancing" nucleic acid sequence which upon expression produces at least one gene product that enhances propagation of a replication-deficient adenoviral vector without necessarily complementing for a deficiency in an adenoviral essential gene function, so as to propagate more replication-deficient adenoviral vectors when present in the cell than when the "enhancing" nucleic acid sequence is absent from the cell. Although genomic integration of this "enhancing" nucleic acid sequence is preferred, the "enhancing" nucleic acid sequence also can be maintained in the cell extrachromosomally (e.g., on a plasmid).

The "enhancing" nucleic acid sequence can be an adenoviral nucleic acid sequence that encodes at least one adenoviral gene product. In particular, the adenoviral gene product can be a protein encoded by, for example, the E1, E2, or E4 regions. The adenoviral gene product also can be a protein encoded by the late regions of the adenoviral genome, such as those encoded by the L1–L5 regions. Alternatively, the "enhancing" nucleic acid sequence can encode the adenoviral IVa2 protein, the pIX protein, or virus-associated RNA (e.g., VA-RNA I or II). The "enhancing" nucleic acid sequence also can be an animal or nonadenoviral nucleic acid sequence. The "enhancing" nucleic acid sequence can encode, for example, an animal protein that inhibits and/or prevents apoptosis (e.g., Bcl-2). Moreover, the "enhancing" nucleic acid sequence can encode, for example, an RNA molecule or protein that improves the efficiency or rate of replication-deficient adenoviral vector propagation.

The expression of the adenoviral nucleic acid sequence in the cell is controlled by a suitable expression control sequence operably linked to the adenoviral nucleic acid sequence. An "expression control sequence" is any nucleic acid sequence that promotes, enhances, or controls expression (typically and preferably transcription) of another nucleic acid sequence. Suitable expression control sequences include constitutive promoters, inducible promoters, repressible promoters, and enhancers. The adenoviral nucleic acid sequence can be regulated by its endogenous promoter or, in contrast, by a nonnative promoter sequence. Examples of suitable nonnative promoters include the CMV immediate early promoter, the phosphoglycerate kinase (PGK) promoter, the long terminal repeat promoter of the Rous sarcoma virus (LTR-RSV), the sheep metallothionien promoter, and the human ubiquitin C promoter. Alternatively, expression of the adenoviral nucleic acid sequence can be controlled by a chimeric promoter sequence. The promoter sequence is "chimeric" when it comprises at least two nucleic acid sequence portions obtained from, derived from, or based upon at least two different sources (e.g., two different regions of an organism's genome, two different organisms, or an organism combined with a synthetic sequence). In addition, the expression control sequence can be activated upon infection with a viral vector, such as a replication-deficient adenoviral vector, or contact with viral peptides. Suitable expression control sequences can be determined using eukaryotic expression systems such as are generally described in Sambrook et al., supra, and by using reporter gene systems (see, e.g., Taira et al., *Gene,* 263, 285–292 (2001)).

The invention also provides a system comprising the inventive cell and a replication-deficient adenoviral vector comprising an adenoviral genome deficient in the at least one essential gene function of the one or more regions (i.e., a replication-deficient adenoviral vector comprising the deficiencies complemented for by the inventive cell). The invention further provides a method of propagating a replication-deficient adenoviral vector. The method comprises providing a cell of the invention, introducing the replication-deficient adenoviral vector into the cell, wherein the replication-deficient adenoviral vector comprises an adenoviral genome deficient in the at least one essential gene function of the one or more regions, and maintaining the cell (e.g., under conditions suitable for adenoviral propagation) to propagate the adenoviral vector.

The adenoviral vector is deficient in at least one gene function (of the adenoviral genome) required for viral propagation (i.e., an adenoviral essential gene function), thereby resulting in a "replication-deficient" adenoviral vector. The adenoviral vector is deficient in the one or more adenoviral essential gene functions complemented for by the inventive cell to allow for propagation of the replication-deficient adenoviral vector when present in the cell.

Preferably, the adenoviral vector is deficient in at least one essential gene function of the E1 region, e.g., the E1a region and/or the E1b region, of the adenoviral genome that is required for viral replication. The recombinant adenovirus also can have a mutation in the major late promoter (MLP), as discussed in International Patent Application WO 00/00628. More preferably, the vector is deficient in at least one essential gene function of the E1 region and at least part of the nonessential E3 region (e.g., an Xba I deletion of the E3 region). The adenoviral vector can be "multiply deficient," meaning that the adenoviral vector is deficient in one or more essential gene functions in each of two or more regions of the adenoviral genome. For example, the aforementioned E1-deficient or E1-, E3-deficient adenoviral vectors can be further deficient in at least one essential gene of the E4 region and/or at least one essential gene of the E2 region (e.g., the E2A region and/or E2B region). Adenoviral vectors deleted of the entire E4 region can elicit lower host immune responses. Examples of suitable adenoviral vectors include adenoviral vectors that lack (a) all or part of the E1 region and all or part of the E2 region, (b) all or part of the E1 region, all or part of the E2 region, and all or part of the E3 region, (c) all or part of the E1 region, all or part of the E2 region, all or part of the E3 region, and all or part of the E4 region, (d) at least part of the E1a region, at least part of the E1b region, at least part of the E2a region, and at least part of the E3 region, (e) at least part of the E1 region, at least part of the E3 region, and at least part of the E4 region, and (f) all essential adenoviral gene products (e.g., adenoviral amplicons comprising ITRs and the packaging signal only). The adenoviral vector can contain a wild type pIX gene. Alternatively, although not preferably, the adenoviral vector also can contain a pIX gene that has been modified by mutation, deletion, or any suitable DNA modification procedure.

The replication-deficient adenoviral vector can be generated by using any species, strain, subtype, or mixture of species, strains, or subtypes, of an adenovirus or a chimeric adenovirus as the source of vector DNA. The adenoviral vector can be any adenoviral vector capable of growth in a cell, which is in some significant part (although not necessarily substantially) derived from or based upon the genome of an adenovirus. The adenoviral vector preferably comprises an adenoviral genome of a wild-type adenovirus of group C, especially of serotype (i.e., Ad5). Adenoviral vectors are well known in the art and are described in, for example, U.S. Pat. Nos. 5,559,099, 5,712,136, 5,731,190, 5,837,511, 5,846,782, 5,851,806, 5,962,311, 5,965,541, 5,981,225, 5,994,106, 6,020,191, and 6,113,913, International Patent Applications WO 95/34671, WO 97/21826, and WO 00/00628, and Thomas Shenk, "Adenoviridae and their Replication," and M. S. Horwitz, "Adenoviruses," Chapters 67 and 68, respectively, in *Virology*, B. N. Fields et al., eds., 3d ed., Raven Press, Ltd., New York (1996).

The construction of adenoviral vectors is well understood in the art and involves the use of standard molecular biological techniques, such as those described in, for example, Sambrook et al., supra, Watson et al., supra, Ausubel et al., supra, and other references mentioned herein. Moreover, adenoviral vectors can be constructed and/or purified using the methods set forth, for example, in U.S. Pat. No. 5,965,358 and International Patent Applications WO 98/56937, WO 99/15686, and WO 99/54441.

When the cell is used to propagate a replication-deficient adenoviral vector, it is desirable to avoid a recombination event between the cellular genome (of the cell) and the adenoviral genome (of the adenoviral vector) that would result in the generation of a replication-competent adenovirus (RCA). As such, there is preferably insufficient overlap between the genome of the cell and the replication-deficient adenoviral vector genome to mediate a recombination event sufficient to result in a replication-competent adenovirus. If overlap exists, the overlapping sequences desirably are predominantly located in the nucleic acid flanking the coding region of the complementation factor (the "trans-complementing region") in the cellular genome and the nucleotide sequences adjacent to the missing region(s) of the adenoviral genome. Ideally, there is no overlap between the cellular genome and the adenoviral vector genome. However, it is acceptable that partial overlap exists between the cellular genome and the adenoviral vector genome on one side of the trans-complementing region. In such an event, the region of homology preferably is contiguous with the trans-complementing region. For example, when the cell comprises a trans-complementing region comprising a nucleotide sequence of the adenoviral E1 region, the cell desirably lacks homologous sequences on the 5' side (left side) of the trans-complementing region corresponding to the adenoviral inverted terminal repeats (ITRs) and packaging signal sequences, but contains homologous sequences on the 3' side (right side) of the trans-complementing region. The region of homology is at least about 2000 base pairs, preferably at least about 1000 base pairs (e.g., at least about 1500 base pairs), more preferably at least about 700 base pairs, and most preferably at least about 300 base pairs.

The cell preferably is characterized by lacking the 5' ITR, the packaging sequence, and the E1A enhancer of the adenoviral genome. The preferred cell is further characterized by desirably comprising the nucleic acid sequences encoding E1A, EB, protein IX, and IVa2/partial E2B. In particular, the preferred cell comprises at least one adenoviral nucleic acid sequence which lacks nucleotides 1–361, yet comprises adenoviral nucleotides 3325–5708 located 3' to the complementing region. Not to adhere to any particular theory, it is believed that a single recombination event in such a homologous region will not give rise to a replication competent adenoviral vector due to the absence of the 5' ITR and packaging sequence. In a similar manner, a preferred cell that contains both the E1 and E4 regions sufficient to propagate E1-, E4-deleted adenoviral vectors can comprise a region of homology between the cellular genome and the adenoviral genome located 5' or 3' to the nucleic acid sequence encoding the E4 region.

The generation of RCA desirably is diminished such that (a) the cell produces less than about one replication-competent adenoviral vector for at least about 20 passages after infection with the adenoviral vector, (b) the cell produces less than about one replication-competent adenoviral vector in a period of about 36 hours post-infection, (c) the cell produces less than about one replication-competent adenoviral vector per $1\times10^{10}$ total viral particles (preferably $1\times10^{11}$ total viral particles, more preferably $1\times10^{12}$ total viral particles, and most preferably $1\times10^{13}$ total viral particles), or any combination of (a)-(c). Optimally, the amount of overlap between the cellular genome and the adenoviral genome (i.e., the genome of the adenoviral vector being propagated in the cell) is insufficient to mediate a homologous recombination event that results in a replication-competent adenoviral vector such that replication-competent adenoviruses are eliminated from the vector stocks resulting from propagation of the replication-deficient adenoviral vector in the cell. Virus growth yield and virus plaque formation have been previously described (see, e.g., Burlseson et al., *Virology: A Laboratory Manual*, Academic Press Inc. (1992)), and measuring RCA as a function of plaque forming units is described in U.S. Pat. No. 5,994,106.

The following examples further illustrate the invention but, of course, should not be construed as in any way limiting its scope.

EXAMPLE 1

This example demonstrates the ability of an NCI-H460 cell and a Calu-1 cell to support high levels of wild-type adenovirus growth.

Calu-1 cells, NCI-H460 (H460) cells, A549 cells (ATCC CCL-185, Manassas, Va.), and 293 cells (Graham et al., supra) were separately cultured using routine tissue culture techniques. Sub-confluent monolayers of each cell culture were infected with wild-type adenovirus 5 (Ad5) at a multiplicity of infection (MOI) of 5. Cells were harvested 48 hours post infection (h.p.i.), and the infected cell lysates were titered for infectious adenovirus by a focus forming unit (FFU) assay (Cleghom et al., *Virology*, 197, 564–575 (1993)). The viral yields of each cell type are set forth in Table 1.

TABLE 1

Wild-type Adenovirus Yield in Cells

| Cell Line | Wild-type Adenovirus Yield (FFU/cell) |
|---|---|
| 293 | 8,511 |
| A549 | 14,638 |
| NCI-H460 | 9,173 |
| Calu-1 | >35,000 |

This example demonstrates the ability of an NCI-H460 cell and a Calu-1 cell to support high levels, e.g., higher than 293 cells or A549 cells, respectively, of wild-type adenovirus production.

EXAMPLE 2

This example describes the construction of an H460 cell and a Calu-1 cell having a cellular genome that comprises an adenoviral E1A coding sequence, an adenoviral E1B coding sequence, and ORF6 (and no other ORF) of the E4 region of the adenoviral genome.

The adenoviral E1 region, corresponding to Ad2 nucleotides 490-3505, is amplified via polymerase chain reaction (PCR) (Innis et al., eds., *PCR Protocols, A Guide to Methods and Applications*, Academic Press, Inc. (1990)) using primers JG104 (5'-GGACTAGTAAGAGGCCACTCTTGAGTG-3' (SEQ ID NO: 1)) and JG105 (5'-AAAAGTACTGGCCGGCCTCAATCTGTATC-3' (SEQ ID NO: 2)). After confirming that the amplified sequences are the expected Ad2 E1 sequence by DNA sequencing, the E1 sequence is cloned between the HIV-15' long terminal repeat (LTR) and the murine μM polyadenylation sequence at the Hpa1/Spe1 cloning sites in the plasmid pHIV.13s.μM.zeo to generate the plasmid pHIV.2E1.μM.zeo. H460 cells and Calu-1 cells are transfected with pHIV.2E1.μM.zeo via the calcium phosphate method and grown under zeocin selection. Zeocin resistant colonies are isolated and propagated under zeocin selection. Northern and Western blotting and mRNA detection assays are performed to detect E1A and E1B expression. Genomic integration of the E1 coding sequences is confirmed via Southern blotting.

The primers A5s(33190)P and A5a(34084)P are used to amplify the ORF-6 region of the Ad5 E4 region by PCR and generate PacI sites at the ends for cloning. The amplified fragment is blunt-ended with Klenow large fragment of DNA polymerase I and cloned into pCR-Script SK(+) (Stratagene, La Jolla, Calif.). The resulting plasmid, pCR/ORF-6, is sequenced. The ORF-6 insert is transferred into the pSMT/puro expression vector, which is generated by ligation of a blunt-ended EcoRI-HindII fragment containing the SMT promoter into the blunt-ended MluI-HindIII site in pRCpuro, to generate pSMT/ORF-6, which also contains the puromycin resistance gene as a selectable marker.

Calu-1 cells and H460 cells containing the pHIV.2E1.μM.zeo plasmid are cultured using standard techniques and transfected with pSMT/ORF-6 via the calcium phosphate method (see, e.g., Sambrook et al., supra). Colonies of transformed cells are subcloned and propagated under puromycin selection for at least 20 passages in culture, to ensure stable retention of the pSMT/ORF-6 construct. Expression of E1A, E1B, and E4-ORF6 gene products is assayed via Northern and Western blotting. Genomic integration of the E1 genes and E4-ORF6 is confirmed via Southern blotting.

EXAMPLE 3

This example describes a method for demonstrating the ability of an NCI-H460 cell and a Calu-1 cell, each comprising the E1 region and ORF-6 of the E4 region of an adenoviral genome, to complement in trans for a deficiency in at least one essential gene function of one or more regions (e.g., E1 and E4) of an adenoviral genome of a replication-deficient adenoviral vector.

The Calu-1 cells and H460 cells of Example 2, which comprise the E1 region and ORF6 of the E4 region of an adenoviral genome, are separately cultured using routine tissue culture techniques. Monolayers at passages 5 and 10 are screened for adenoviral E1 and E4 region gene function complementation by a virus production assay (see, e.g., Burlseson et al., *Virology: A Laboratory Manual*, Academic Press Inc. (1992)). In that respect, cells are separately infected with wild-type adenovirus 5 and a replication-deficient adenoviral vector (AdRSVβ-gal. 11) wherein the E1 and E4 regions have been deleted from the adenoviral genome thereof (Brough et al., *J. Virol.*, 70, 6497–6501 (1996)). Specifically, the cells are infected with AdRSVβ-gal. 11 at a multiplicity of infection (MOI) of 10. Cell lysates are prepared at 3 days post-infection (d.p.i.), and the amount of active virus in the lysates is determined by a focal forming unit (FFU) assay (Cleghom et al., *Virology*, 197, 564–575 (1993)). The detection of significant yields of AdRSVβ-gal.11 for each cell line at passages 5 and 10 evidences the ability of the cell line to complement in trans for deficiencies in adenoviral essential gene functions of the E1 and E4 regions of the adenoviral genome.

invention unless otherwise indicated herein or otherwise clearly contradicted by context.

```
                         SEQUENCE LISTING

<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: Synthetic sequence used as PCR primer.

<400> SEQUENCE: 1
ggactagtaa gaggccactc ttgagtg                                          27

<210> SEQ ID NO 2
<211> LENGTH: 29
<212> TYPE: DNA
<213> ORGANISM: Artificial Sequence
<220> FEATURE:
<223> OTHER INFORMATION: Synthetic sequence used for PCR primer.

<400> SEQUENCE: 2
aaaagtactg gccggcctca atctgtatc                                        29
```

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Of course, variations of those preferred embodiments will become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the

What is claimed is:

1. An NCI-H460 cell having a cellular genome comprising at least one adenoviral nucleic acid sequence, which upon expression produces a gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell.

2. The cell of claim 1, wherein the one or more regions of the adenoviral genome are selected from the group consisting of the E1, E2, and E4 regions.

3. The cell of claim 1, wherein the adenoviral nucleic acid sequence comprises an adenoviral E1A coding sequence and an adenoviral E1B coding sequence.

4. The cell of claim 1, wherein the one or more regions of the adenoviral genome are the E1 region and at least one additional region.

5. The cell of claim 4, wherein the at least one additional region comprises the E4 region.

6. The cell of claim 5, wherein the cellular genome comprises at least ORF6 of the E4 region of the adenoviral genome.

7. The cell of claim 6, wherein the cellular genome comprises at least ORF6 and no other ORF of the E4 region of the adenoviral genome.

8. A Calu-1 cell having a cellular genome comprising at least one adenoviral nucleic acid sequence, which upon expression produces a gene product that complements in trans for a deficiency in at least one essential gene function of one or more regions of an adenoviral genome so as to propagate a replication-deficient adenoviral vector comprising an adenoviral genome deficient in the at least one essential gene function of the one or more regions when present in the cell.

9. The cell of claim 8, wherein the one or more regions of the adenoviral genome are selected from the group consisting of the E1, E2, and E4 regions.

10. The cell of claim 8, wherein the adenoviral nucleic acid sequence comprises an adenoviral E1A coding sequence and an adenoviral E1B coding sequence.

11. The cell of claim 8, wherein the one or more regions of the adenoviral genome are the E1 region and at least one additional region.

12. The cell of claim 11, wherein the at least one additional region comprises the E4 region.

13. The cell of claim 12, wherein the cellular genome comprises at least ORF6 of the E4 region of the adenoviral genome.

14. The cell of claim 13, wherein the cellular genome comprises at least ORF6 and no other ORF of the E4 region of the adenoviral genome.

* * * * *